(12) United States Patent
Lynn

(10) Patent No.: US 10,709,273 B1
(45) Date of Patent: Jul. 14, 2020

(54) UTENSIL APPARATUS

(71) Applicant: Jason Lynn, Ferndale, MI (US)

(72) Inventor: Jason Lynn, Ferndale, MI (US)

(*) Notice: Subject to any disclaimer, the term of this patent is extended or adjusted under 35 U.S.C. 154(b) by 0 days.

(21) Appl. No.: 16/601,895

(22) Filed: Oct. 15, 2019

(51) Int. Cl.
*A47G 21/08* (2006.01)
*A61F 4/00* (2006.01)

(52) U.S. Cl.
CPC ........ *A47G 21/08* (2013.01); *A47G 2200/046* (2013.01); *A61F 4/00* (2013.01)

(58) Field of Classification Search
CPC .. A47G 21/08; A47G 2200/046; A46B 17/02; A61F 4/00; A61F 2/588; B43K 23/001; B43K 23/004; B43L 15/00
USPC ......... 294/25; 224/218; 30/323, 327; 623/65
See application file for complete search history.

(56) References Cited

U.S. PATENT DOCUMENTS

| | | | |
|---|---|---|---|
| 552,171 A * | 12/1895 | Farnham | |
| 2,278,610 A * | 4/1942 | Brownson | A01D 11/00 294/25 |
| 2,889,160 A * | 6/1959 | Nelson | A61F 2/583 403/93 |
| 3,503,546 A | 3/1970 | Hunt | |
| 3,942,194 A * | 3/1976 | Winter | A47G 21/08 623/65 |
| 4,035,865 A | 7/1977 | McRae et al. | |
| 4,165,896 A | 8/1979 | Hunt | |
| 4,325,187 A | 4/1982 | Wasson | |
| 4,447,912 A | 5/1984 | Morrow | |
| 4,606,484 A | 8/1986 | Winter et al. | |
| 4,944,766 A | 7/1990 | Williams | |
| 5,060,386 A | 10/1991 | Mars | |
| 5,068,967 A | 12/1991 | Mars | |
| 5,542,588 A * | 8/1996 | Sison | B43K 23/001 15/443 |
| 5,597,189 A | 1/1997 | Barbee, Sr. | |
| 5,779,292 A | 7/1998 | Kasday | |
| 5,791,705 A | 8/1998 | Romero et al. | |
| 5,853,210 A | 12/1998 | Robinson | |
| 5,860,190 A | 1/1999 | Cano | |
| 6,394,516 B1 | 5/2002 | Zhuraysky | |
| 6,702,496 B1 * | 3/2004 | Park | B43K 23/001 224/267 |
| 8,468,700 B2 | 6/2013 | Wilson | |

(Continued)

FOREIGN PATENT DOCUMENTS

| | | | | |
|---|---|---|---|---|
| CA | 2917929 A1 * | 1/2015 | ............ | A61F 5/0118 |
| JP | 2002085486 A | 3/2002 | | |

*Primary Examiner* — Dean J Kramer
(74) *Attorney, Agent, or Firm* — Fishman Stewart PLLC

(57) ABSTRACT

A utensil apparatus includes a body, a first end portion, and a second end portion. The body may include an aperture that may be configured to receive a utensil. The first end portion may extend from the body, and/or the second end portion may extend from the body. The aperture may be configured to receive at least a portion of the utensil such that the utensil may extend through the aperture. The body may be substantially planar, and/or the first end portion may be configured to engage the second end portion to connect the body to a hand of a user. The body may include a first portion, a second portion, and/or a second aperture. The second portion may be disposed at least partially in the second aperture. The second portion may be configured to rotate within the second aperture to hold the utensil in a plurality of positions.

20 Claims, 14 Drawing Sheets

(56) References Cited

U.S. PATENT DOCUMENTS

| 8,840,157 | B2* | 9/2014 | Dempsey | A46B 5/025 |
| | | | | 294/25 |
| 2007/0012736 | A1* | 1/2007 | Wagner | A45F 5/00 |
| | | | | 224/218 |
| 2017/0290451 | A1 | 10/2017 | Flesher | |

* cited by examiner

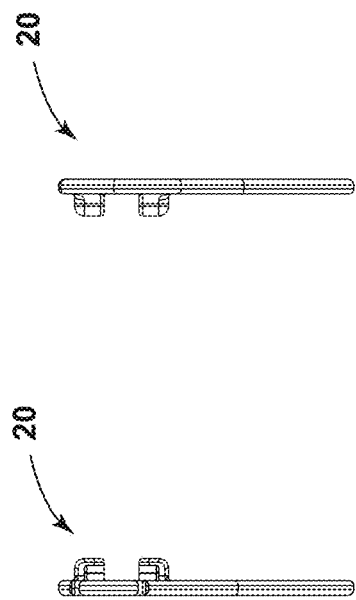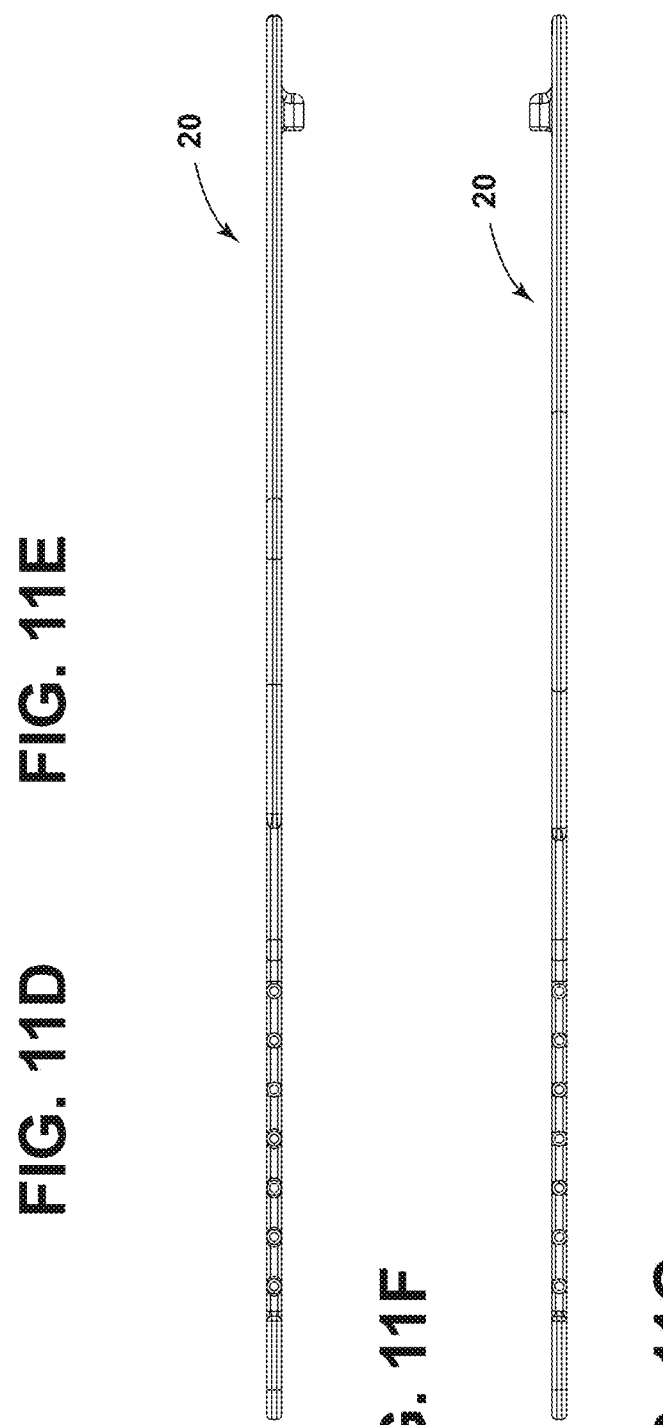
FIG. 11D  FIG. 11E  FIG. 11F  FIG. 11G

UTENSIL APPARATUS

TECHNICAL FIELD

The present disclosure generally relates to utensil apparatuses, including utensil apparatuses that may be used in connection with a hand of a user.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Some utensil apparatuses may be relatively complex to use and/or assemble, and may not include sufficient functionality.

There is a desire for solutions/options that minimize or eliminate one or more challenges or shortcomings of utensil apparatuses. The foregoing discussion is intended only to illustrate examples of the present field and is not a disavowal of scope.

SUMMARY

In embodiments, a utensil apparatus may include a body, a first end portion, and/or a second end portion. The body may include an aperture that may be configured to receive a utensil. The first end portion may extend from the body, and/or the second end portion may extend from the body. The aperture may be configured to receive at least a portion of said utensil such that said utensil may extend through the aperture. The body may be substantially planar, and/or the first end portion may be configured to engage the second end portion to connect the body to a hand of a user. The body may include a first portion, a second portion, and/or a second aperture. The second portion may be disposed at least partially in the second aperture. The second portion may be configured to rotate within the second aperture to hold said utensil in a plurality of positions.

With embodiments, the aperture may be offset from the second aperture in a first direction and/or a second direction. The second portion may include a third aperture, and/or the third aperture may be configured to at least partially receive said utensil. The third aperture may be substantially X-shaped. The third aperture may be substantially triangular. The second portion may include a channel that may be configured to at least partially receive a radial flange of the first portion for rotatably connecting the second portion with the first portion. The channel may be at least partially defined between a first flange portion of the second portion and a second flange portion of the second portion. The first flange portion may include a smaller diameter than the second flange portion. The body may be configured to move between a first configuration and/or a second configuration. The body may be substantially flat in the first configuration, and/or the body may be substantially oval-shaped in the second configuration.

In embodiments, the first end portion may include a plurality of teeth, and/or the second end portion may include an engagement portion. At least one of the plurality of teeth may be configured to engage the engagement portion to maintain the utensil apparatus in the second configuration. The utensil apparatus may be reversible for use with right and/or left hands of users. The utensil apparatus may include a plurality of interchangeable disks configured for selective connection with the body via the aperture. The utensil apparatus may include a flange member that may be configured to selectively connect to the first end portion. The first end portion may include a connection section. The flange member may be configured to connect to the connection section. The flange member may include a utensil connection portion and/or a flange aperture. The flange aperture may be configured to receive the first end portion, and/or the utensil connection portion may be configured to at least partially receive said utensil.

With embodiments, a utensil apparatus may include a body, a first end, and/or a second end. The body may include a plurality of apertures. A method of operating a utensil apparatus may include connecting the first end to the second end such that the body may be connected to a hand of a user. The method may include inserting at least a portion of a utensil through at least one of the plurality of apertures such that the utensil may extend at least partially beyond the body. The plurality of apertures may include a first aperture and/or a second aperture. The first portion of the body may include the first aperture and/or the second aperture. A second portion of the body may be disposed in the second aperture. The second portion may include a third aperture of the plurality of apertures. The third aperture may be configured to receive said utensil, and/or the second portion may be configured to rotate within the second aperture to hold the utensil in a plurality of positions. Inserting at least the portion of the utensil through the at least one of the plurality of apertures may include inserting the portion of the utensil through the second aperture and/or the third aperture. The method may include rotating the second portion in the second aperture, which may provide a different use angle for the utensil.

The foregoing and other aspects, features, details, utilities, and/or advantages of embodiments of the present disclosure will be apparent from reading the following description, and from reviewing the accompanying drawings.

BRIEF DESCRIPTION OF THE DRAWINGS

FIG. 11D is a side view of the embodiment of a utensil apparatus of FIG. 11A.

FIG. 11E is a side view of the embodiment of a utensil apparatus of FIG. 11A.

FIG. 11F is a top view of the embodiment of a utensil apparatus of FIG. 11A.

FIG. 11G is a bottom view of the embodiment of a utensil apparatus of FIG. 11A.

DETAILED DESCRIPTION

Reference will now be made in detail to embodiments of the present disclosure, examples of which are described herein and illustrated in the accompanying drawings. While the present disclosure will be described in conjunction with embodiments and/or examples, they do not limit the present disclosure to these embodiments and/or examples. On the contrary, the present disclosure covers alternatives, modifications, and equivalents.

Figure 1:
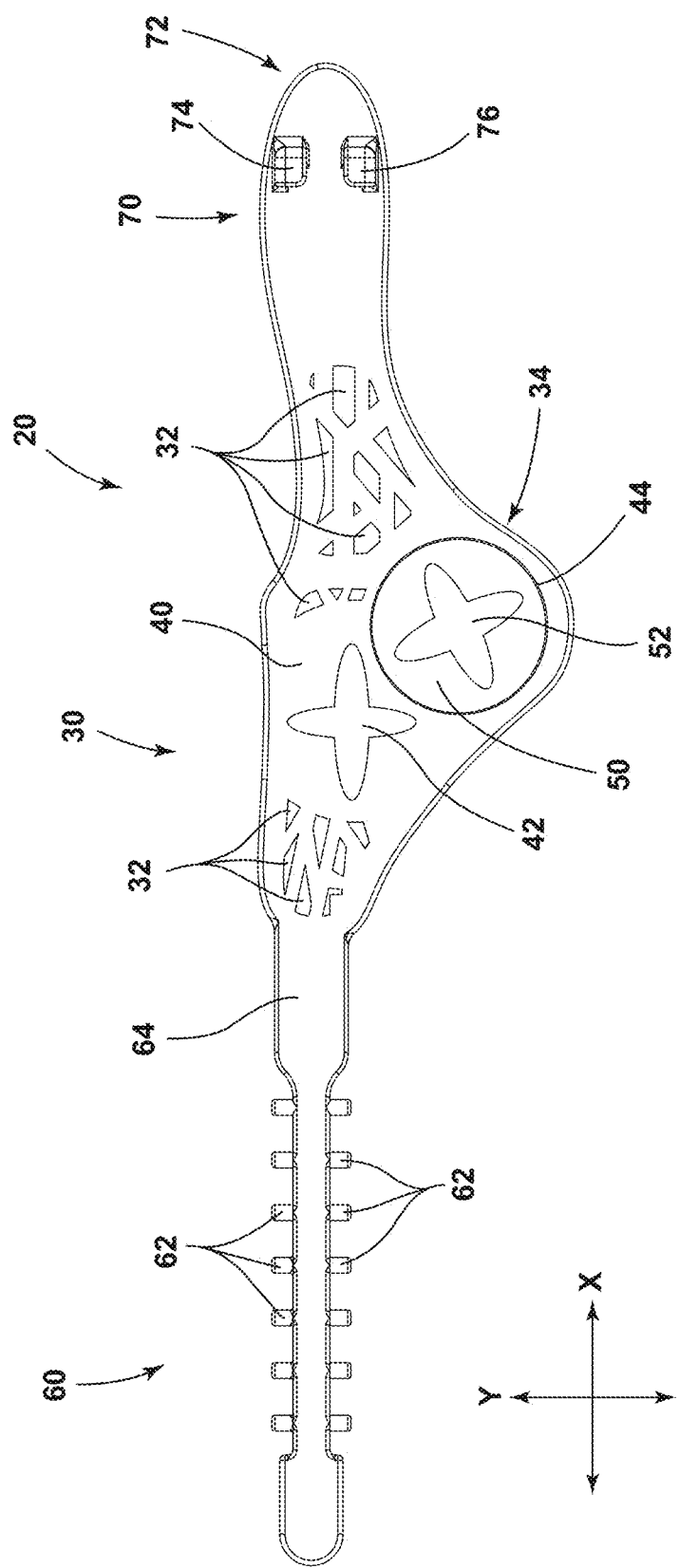
FIG. 1 is a top view generally illustrating an embodiment of a utensil apparatus in a first configuration according to teachings of the present disclosure.
Figure 2A:
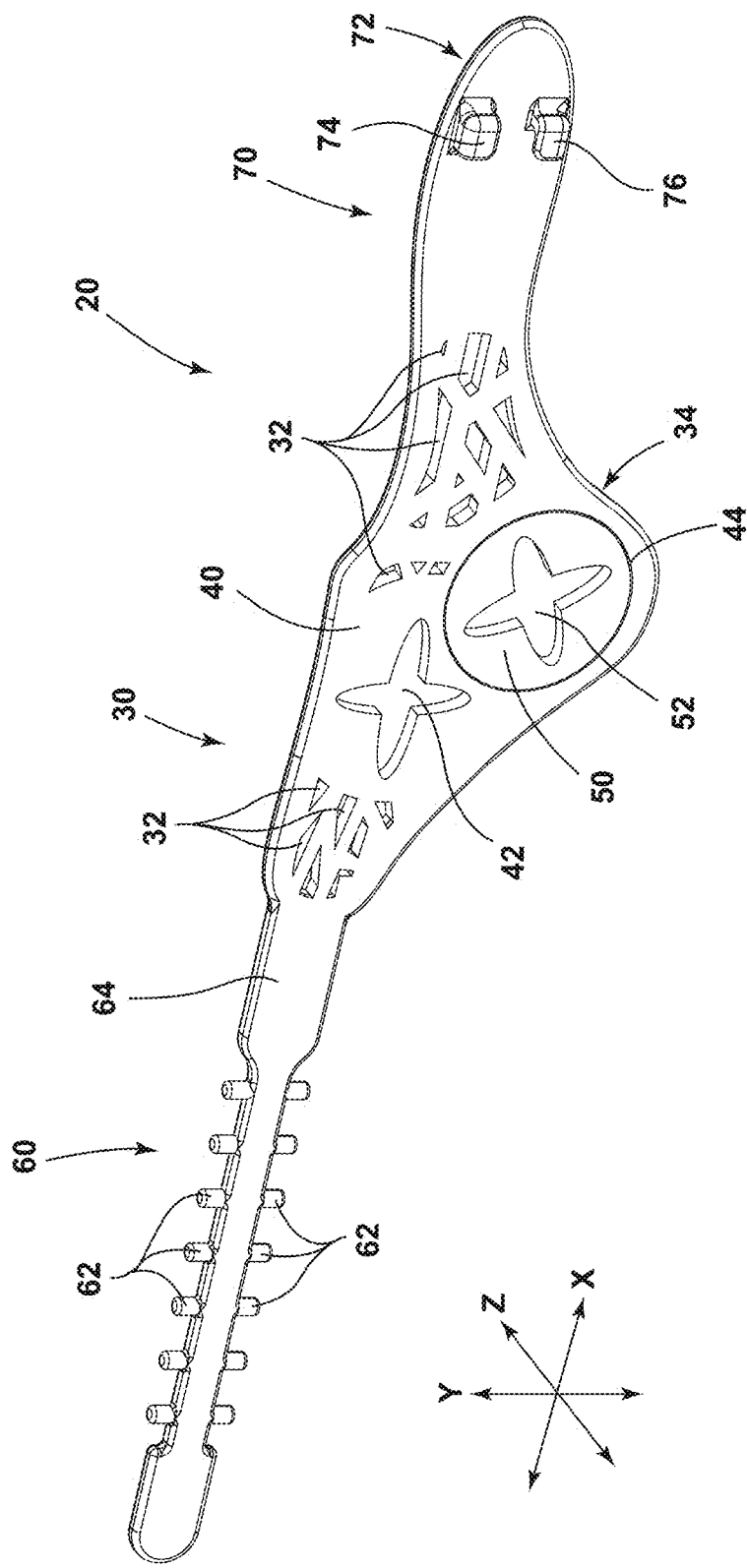
FIG. 2A is a perspective view generally illustrating an embodiment of a utensil apparatus in a first configuration according to teachings of the present disclosure.

In examples, such as generally illustrated in FIGS. 1 and 2A, a utensil apparatus 20 may include a body 30, a first end portion 60, and/or a second end portion 70. The utensil apparatus 20 may be configured to for connection with a utensil 22 and/or a hand 10 of a user (see, e.g., FIG. 5). For example and without limitation, a utensil apparatus 20 may be configured to support (e.g., hold, retain, maintain, etc.) and/or facilitate support of a utensil 22 in the hand 10 of a user. The utensil apparatus 20 may be configured to contact a hand 10 of a user. The utensil apparatus 20 may be configured to stabilize and/or receive a utensil 22. The utensil apparatus 20 may substantially limit movement of the utensil 22 in at least one direction. The utensil apparatus 20 may include a first configuration (see, e.g., FIGS. 1 and 2A) and/or a second configuration (see, e.g., FIGS. 5 and 6). When the utensil apparatus 20 is in the first configuration, the utensil apparatus 20 may, for example, be substantially flat. When the utensil apparatus 20 is in the second configuration, the utensil apparatus 20 may, for example, be configured to support a utensil 22 in the hand 10 of a user and/or in a variety of other configurations.

With examples, such as generally illustrated in FIGS. 1 and 2A, a utensil apparatus 20 may include a body 30. The body 30 may be configured to contact a utensil 22 and/or substantially limit movement of a utensil 22. For example and without limitation, the body 30 may be configured to facilitate holding a utensil 22 for a user that may have reduced control of at least one hand 10 of the user. The body 30 may include one or more of a variety of shapes, sizes, and/or configurations. For example and without limitation, the body 30 may be substantially triangular. For example and without limitation, the body 30 may be configured to be disposed at or near the base of the fingers of a hand 10 and extend away from the fingers in a direction generally parallel with the arm of the user. The body 30 may include one or more of a variety of materials. For example and without limitation, the body 30 may include a polymer material (e.g., plastic). The body 30 may include a material that may be configured to bend and/or flex, at least to some degree, which may facilitate moving the utensil apparatus 20 between the first configuration and the second configuration. Additionally or alternatively, the body 30 may include a material that may be sufficiently rigid to hold a utensil 22 when connected to a hand 10 of a user. The body 30 may include a plurality of formations 32. The formations 32 may, for example and without limitation, include apertures that may be configured to provide structural support for the utensil apparatus 20 and/or to reduce the overall weight of the utensil apparatus 20. The plurality of formations 32 may include one or more of a variety of shapes, sizes, and/or configurations. For example and without limitation, the plurality of formations 32 may be triangular, rectangular, and/or polygonal. The plurality of formations 32 may be disposed on a first side and/or a second side of the body 30.

In examples, such as generally illustrated in FIGS. 1, 2A, 3, and 4A, the body 30 may include a first portion 40 and/or a second portion 50. The first portion 40 may include one or more of a variety of shapes, sizes, and/or configurations. For example and without limitation, the first portion 40 may be substantially triangular. The first portion 40 may include a first aperture 42 and/or a second aperture 44.

With exemplary embodiments, the first aperture 42 of the body 30 may be configured to at least partially receive a utensil 22 (e.g., a handle portion/end 24 of a utensil 22). The first aperture 42 may be configured such that an end of a utensil 22 may extend completely through first aperture 42 and/or may at least partially contact a hand 10/palm 12 of a user (see, e.g., FIGS. 5 and 6). For example and without limitation, the hand 10/palm 12 of a user may limit an insertion depth of the utensil 22 and/or may limit movement of the utensil 22, at least to some degree. The first aperture 42 may include one or more of a variety of shapes, sizes, and/or configurations. The first aperture 42 may, for example and without limitation, be substantially T-shaped, X-shaped, and/or triangular. The shape of the first aperture 42 may be such that a planar portion/end of a utensil 22 may be inserted into the first aperture 42. The shape of the first aperture 42 may be such that the first aperture 42 may substantially limit movement of a utensil 22 in at least one direction. The first aperture 42 may substantially limit the utensil 22 from disengaging from the body 30 (e.g., the first portion 40). The first aperture 42 may be configured to receive a utensil 22 in one or more of a variety of orientations. For example and without limitation, a utensil 22 may be inserted into the second aperture 44 with a variety of angular orientations, such as first and second orientations that may be offset by about 90 degrees (e.g., relative to an axis extending perpendicular to the body 30). In a connected position of the utensil 22 with the utensil apparatus 20, the utensil 22 may be disposed at an oblique or right angle with respect to some or most of the body 30. The utensil apparatus 20 may be configured to retain a utensil 22 in a variety of angular positions. For example and without limitation, a user may operate the utensil apparatus 20 in a variety of different hand positions. The first aperture 42 and/or the second aperture 44 may be configured to retain a utensil 22 for use in the variety of different hand positions.

Figure 5:
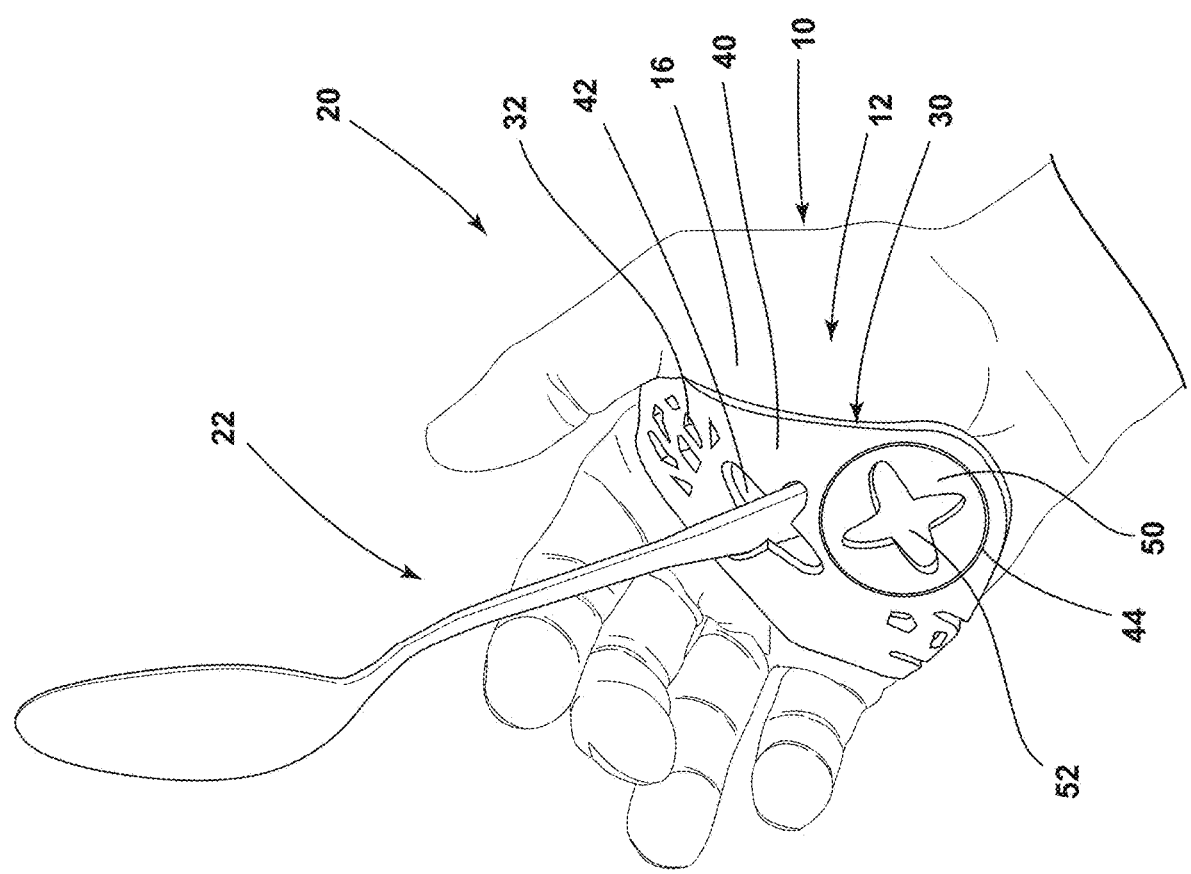
FIG. 5 is a perspective view generally illustrating an embodiment of a utensil apparatus in a second configuration connected to a hand and a utensil according to teachings of the present disclosure.

In examples, the second aperture 44 may be configured to at least partially receive the second portion 50 and/or a utensil 22 (e.g., a handle portion/end 24 of a utensil 22, such as generally illustrated in FIG. 5). The second aperture 44 may be disposed in a protruding portion 34 of the body 30. The protruding portion 34 may, for example, be configured to abut the palm 12 of a user at or near the base of the thumb 16. The second aperture 44 may, for example, be substantially circular. The second portion 50 of the body 30 may be configured to rotate within the first portion 40 of the body 30 (e.g., within the second aperture 44).

Figure 7C:
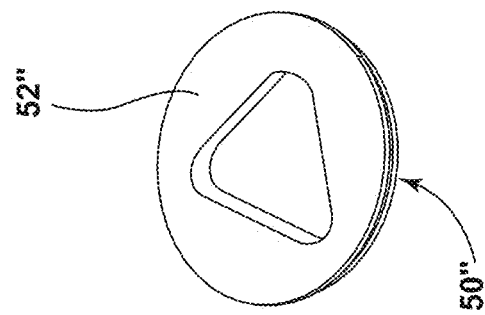
FIGS. 7A, 7B, and 7C are perspective views generally illustrating portions of embodiments of second portions of a body of a utensil apparatus according to teachings of the present disclosure.
Figure 7B:
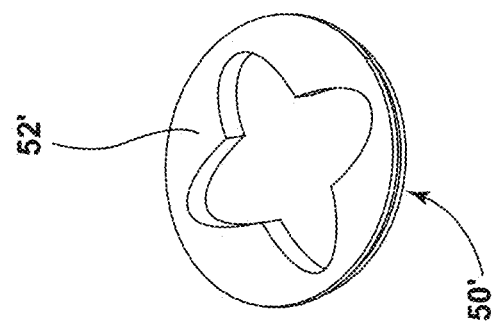
Figure 7A:
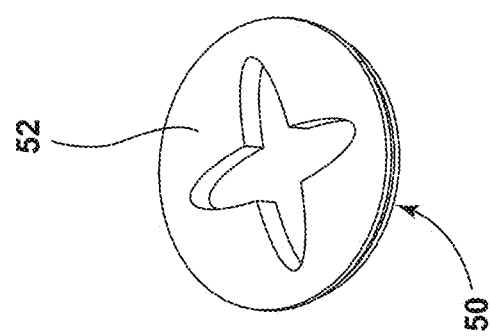

In examples, such as generally illustrated in FIGS. 1, 2A, 4A, and 5, a utensil apparatus 20 may include a second portion 50. The second portion 50 may be at least partially disposed in the second aperture 44 of the body 30. The second portion 50 may be rotatably connected with the first portion 40 of the body 30. The second portion 50 of the body 30 may be configured to rotatably support a utensil 22. The second portion 50 may rotate such as to change the position of a utensil 22 relative to the body 30 and/or relative to the hand 10 of a user. For example and without limitation, the second portion 50 may rotate and/or retain a utensil 22 at a plurality of angular positions and/or rotational positions. A user may insert a utensil 22 into the second portion 50 of the body 30 and/or the user may adjust the position of the utensil 22 while the utensil 22 may be engaged with the utensil apparatus 20 (e.g., a user may rotate a utensil 22 in the second portion 50 to rotate the second portion 50 within the aperture 42 to provide different utensil use angles). The second portion 50 of the body 30 may include one or more of a variety of shapes, sizes, and/or configurations. For example and without limitation, the second portion 50 may be substantially planar and/or circular, and/or may include a disk configuration. The second portion 50 may include an aperture 52 for receiving and/or substantially limiting movement of a utensil 22. The aperture 52 of the second portion 50 may include one or more of a variety of shapes, sizes, and/or configurations (see, e.g., FIGS. 7A, 7B, 7C). For example and without limitation, the aperture 52 may be substantially rounded, X-shaped (see, e.g., second portions 50, 50' and apertures 52, 52' in FIGS. 7A and 7B), T-shaped, and/or triangular (see, e.g., second portion 50" and aperture 52" in FIG. 7C). A utensil apparatus 20 may include one or a plurality of second portions 50, 50', 50" that may be configured as interchangeable disks configured for selective connection with the body 30. The shape of the aperture 52 may be such that a portion (e.g., a planar end) of a utensil 22 may be inserted into the aperture 52. The planar end of a utensil 22 may contact an inner surface of the aperture 52. A utensil 22 may be inserted into the aperture 52 (see, e.g., FIG. 5) and/or the planar end of the utensil 22 may extend through the aperture 52 and contact the hand 10 of a user (e.g., a palm 12 of a user). Contact between the utensil 22 and the inner surface of the aperture 52, and/or contact between the utensil 22 and the palm 12 of a user may substantially retain the utensil 22 (e.g., movement of the utensil 22 may be substantially limited). In a connected configuration of a second portion 50, the second portion 50 may, for example, be substantially flush with one or both sides of the body 30.

Figure 4A:
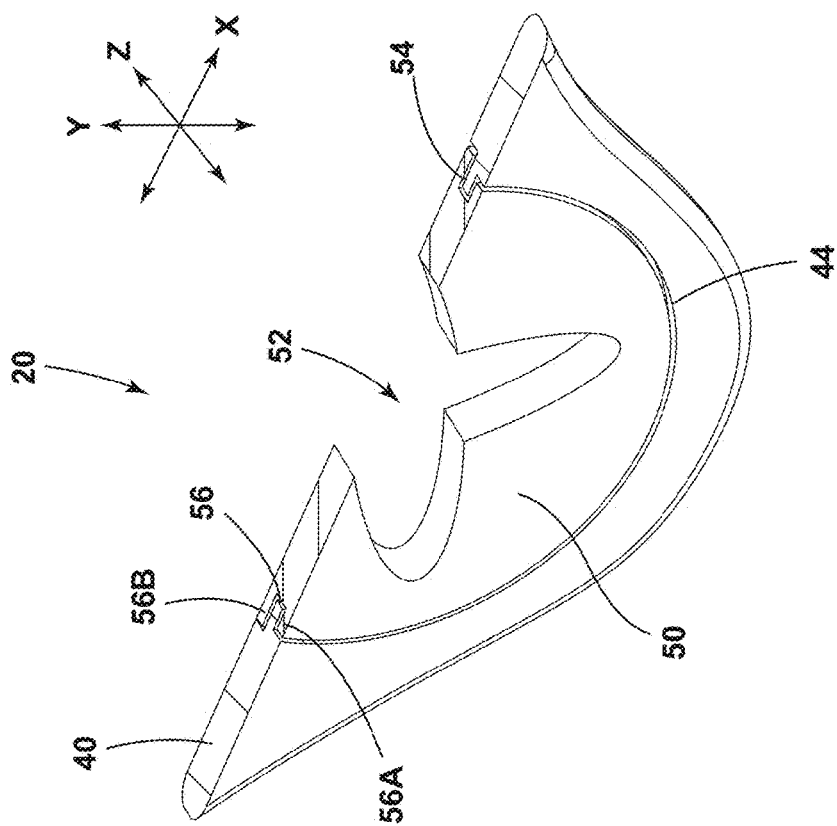
FIG. 4A is a cross-sectional perspective view generally illustrating portions of an embodiment of a utensil apparatus according to teachings of the present disclosure.
Figure 3:
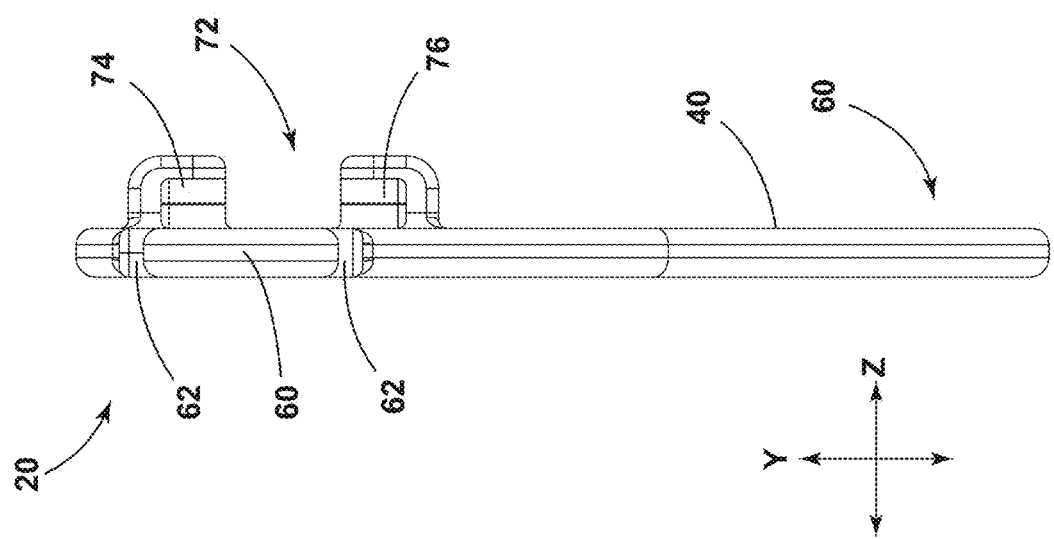
FIG. 3 is a side view generally illustrating an embodiment of a utensil apparatus in a first configuration according to teachings of the present disclosure.
Figure 6:
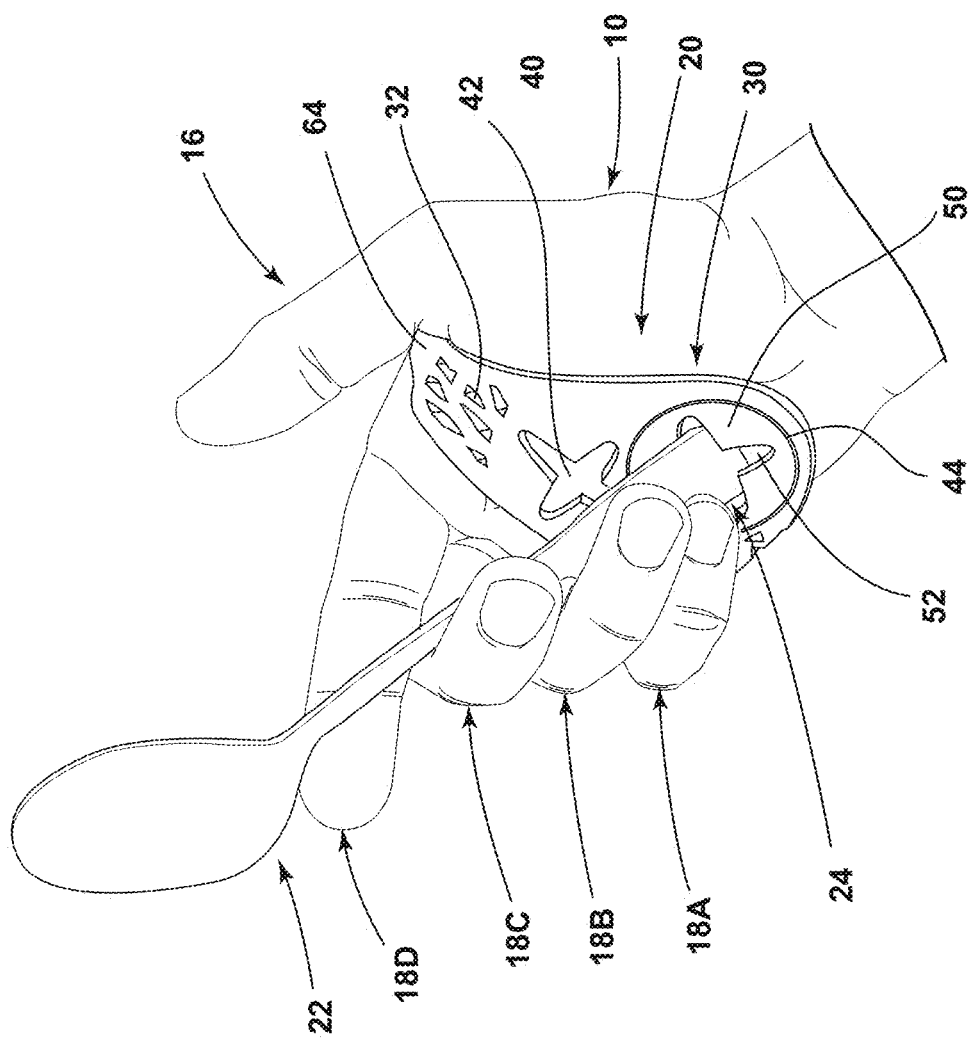
FIG. 6 is a perspective view generally illustrating an embodiment of a utensil apparatus in a second configuration connected to a hand and a utensil according to teachings of the present disclosure.

With embodiments, such as generally illustrated in FIGS. 4A and 6, the second portion 50 of the body 30 may be rotatably connected with the first portion 40 of the body 30, such as via the second aperture 44 (additionally or alternatively, the first portion 40 may be rotatably connected to the second portion 50 in the same or substantially similar manner as the second portion 50 may be rotatably connected to the first portion 40). The second aperture 44 of the body 30 may include a radial flange 54 that may extend from an inner surface of the second aperture 44 (see, e.g., FIG. 4A). The radial flange 54 may include a thickness that may be less than a thickness of the body 30 and/or less than a thickness of the second portion 50. The radial flange 54 may be configured to be at least partially received by the second portion 50.

With examples, the second portion 50 may include a channel 56 that may extend about an outer radial surface of the second portion 50. The channel 56 and/or the radial flange 54 may be configured to rotatably connect the second portion 50 to the first portion 40 of the body 30. The channel 56 may be formed, at least in part via a first flange portion 56A and/or a second flange portion 56B (e.g., radially-extending flange portions).

Figure 4D:
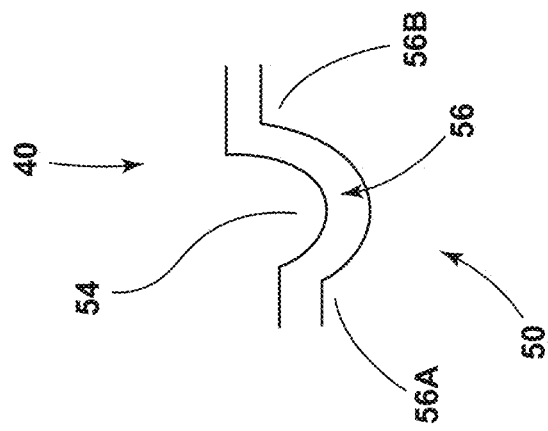
FIGS. 4B, 4C, and 4D are perspective views generally illustrating portions of embodiments of a utensil apparatus according to teachings of the present disclosure.
Figure 4C:
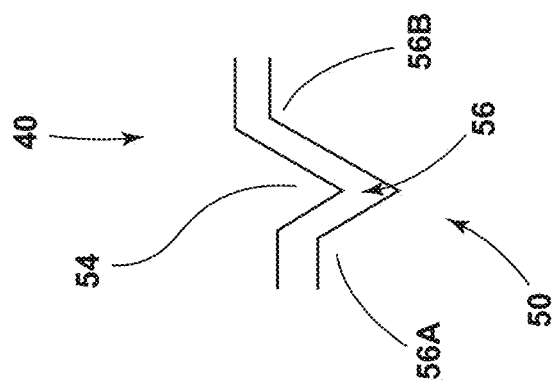
Figure 4B:
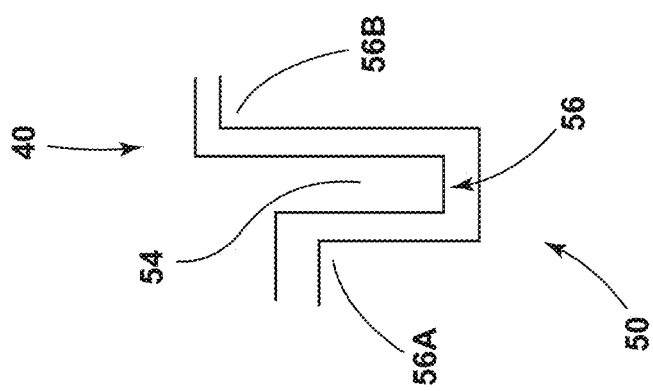

In examples, the second portion 50 may be selectively removable from the first portion 40 of the body 30. For example, the first flange portion 56A may include a first diameter and the second flange portion 56B may include a second diameter. The first diameter may be less than the second diameter such that the second portion 50 may be removed (e.g., disengaged) from the first portion 40 in a first direction (e.g., towards the second flange portion 56B) and/or connected with the first portion 40 in a second direction (e.g., toward the first flange portion 56A). At least one of the first flange portion 56A of the second portion 50 and the radial flange 54 of the first portion 40 may be flexible, at least to some degree, which may permit the radial flange 54 of the first portion 40 to snap into the channel 56 of the second portion 50. The outer diameter of the channel 56 and the inner diameter of the radial flange 54 may be substantially similar such that relative movement of the second portion 50 in the second aperture 44 may be restricted (e.g., to limit movement of/provide stability for a connected utensil 22), but may not be prevented (e.g., a user may cause relative rotation by applying a rotational force greater and a frictional force between the first portion 40 and the second portion 50). A profile of the first portion 40 may be complementary to a profile of the second portion 50 such that the first portion 40 may be configured to receive the second portion 50 and/or limit movement of the second portion 50 in at last one direction. The first portion 40 and the second portion 50 may include profiles of a variety of shapes, sizes, and/or configurations. For example and without limitation, the first portion 40 and/or the second portion 50 may include rectangular, triangular, conical, and/or curved profiles (see, e.g., FIGS. 4B, 4C, and 4D).

With examples, a utensil apparatus 20 may include one or more of a variety of second portions 50. For example and without limitation, second portions 50 may be configured to be selectively engaged with the first portion 40 to connect a variety of utensils 22 with the utensil apparatus 20. The second portion 50 of the utensil apparatus 20 may be replaced with one or more other second portions (e.g., second portions 50', 50" generally illustrated in FIGS. 7B and 7C), which may be configured to connect a variety of utensils 22 to the utensil apparatus 20.

In examples, the first aperture 42 and the second aperture 44 may be offset from each other, at least to some degree, such as in a first direction and a second direction. For example and without limitation, the centers of first aperture 42 and the second aperture 44 may be offset in the X-direction and/or the Y-direction. Portions of the first aperture 42 and the second aperture 44 may overlap in the X-direction and/or the Y-direction. The first aperture 42 and/or the second aperture 44 may be disposed such that in the second configuration of the body 30, the first aperture 42 and/or the second aperture 44 may be at least partially aligned with a palm 12 of a user.

With examples, a utensil apparatus 20 may include a first end portion 60 and/or a second end portion 70. The first end portion 60 and/or the second end portion 70 may extend from the body 30 of the utensil apparatus 20, such as in the X-direction (see, e.g., FIGS. 1 and 2A). The first end portion 60 and/or the second end portion 70 may be configured to engage each other to connect the utensil apparatus 20 with a hand 10 of a user. The utensil apparatus 20 may include a first configuration and/or a second configuration. The first end portion 60 and the second end portion 70 may facilitate changing between a first configuration and/or a second configuration. The body 30, including the first end portion 60 and/or the second end portion 70, may be formed as a monolithic component. The body 30, the first end portion 60, and/or the second end portion 70 may be configured to interact and engage a hand 10 of a user (see, e.g., FIG. 8).

With embodiments, the first end portion 60 may be configured to engage with the second end portion 70 in one or more of a variety of ways, such as to connect the utensil apparatus 20 with a hand 10 of a user. For example and without limitation, the first end portion 60 may include a latching element (e.g., a clasp, latch, teeth, etc.) that may be configured to engage the second end portion 70. Additionally or alternatively, the second end portion 70 may include a latching element that may be configured to engage the first end portion 60.

In embodiments, the first end portion 60 may be substantially elongated and/or may extend from the body 30. The first end portion 60 may include a plurality of teeth 62. The plurality of teeth 62 may extend from the first end portion 60 substantially in the Y-direction. The plurality of teeth 62 may extend from the first end portion 60 in a first direction and/or a second direction. The first direction may be opposite the second direction (e.g., opposite Y-directions). The plurality of teeth 62 may be configured to at least partially engage the second end portion 70. The first end portion 60 may include a flexible/elastic material such that the first end portion 60 may be configured to bend (e.g., around the hand 10 of a user to engage the second end portion 70).

With embodiments, the first end portion 60 may include a connection section 64 (see, e.g., FIGS. 1 and 2A). The connection section 64 may be disposed between the plurality of teeth 62 of the first end portion 60 and the body 30. The connection section 64 may include one or more of a variety of shapes, sizes, and/or configurations. The connection section 64 may be substantially rectangular shaped. The connection section 64 may not include teeth 62, and/or the connection section 64 may be substantially planar.

Figure 2B:
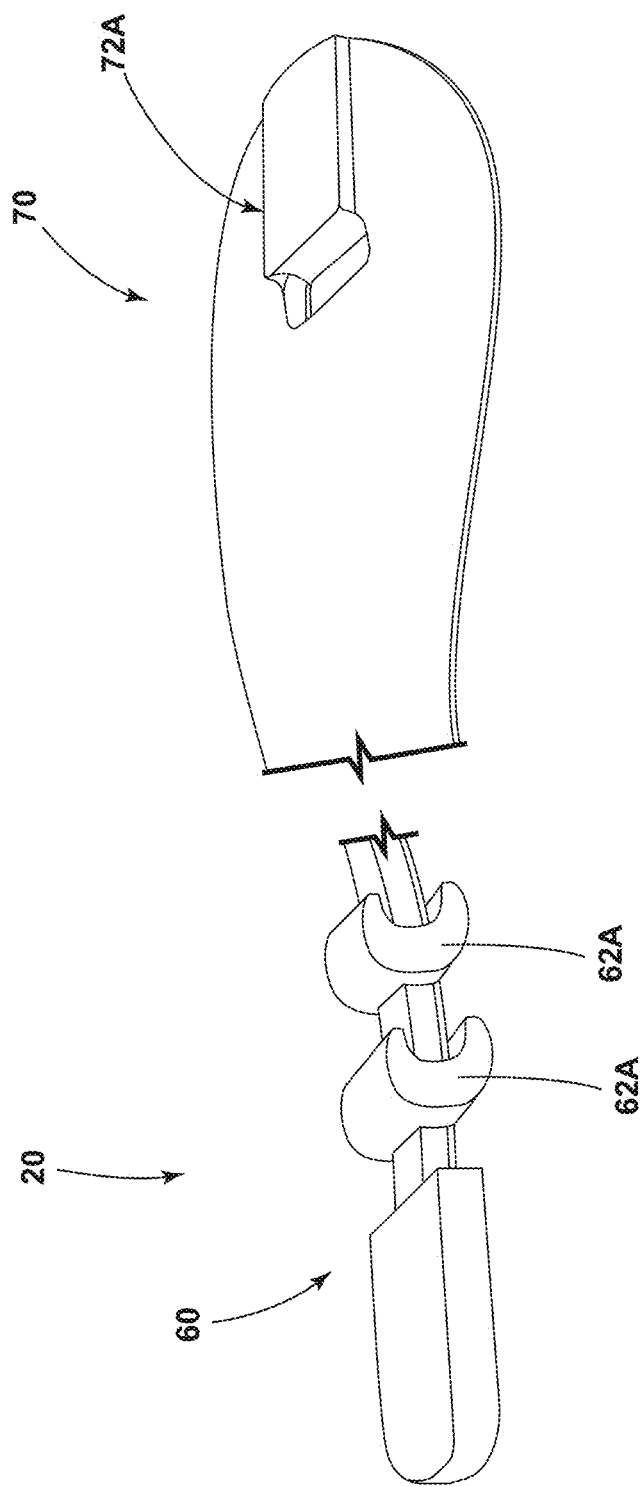
FIG. 2B is a perspective views generally illustrating portions of an embodiment of a utensil apparatus according to teachings of the present disclosure.

In embodiments, such as generally illustrated in FIG. 2B, the first end portion 60 may include one or more hooks 62A that may be configured to selectively engage one or more recesses/apertures 72A. The one or more hooks 62A may include one or more of a variety of shapes, sizes, and/or configurations. For example and without limitation, the hooks 62A may be curved, rounded, and/or C-shaped. A shape of the hook 62A may be substantially complementary to the shape of the recess 72A. The recess 72A may be substantially rectangular, circular, and/or rounded. The recess 72A may be configured to receive at least a portion of the first end portion 60. One or more hooks 62A of the first end portion 60 may be configured to contact an edge and/or an inner surface of the recess 72A to retain the utensil apparatus 20 in the second configuration.

With embodiments, the second end portion 70 may be substantially elongated. The second end portion 70 may include an engagement portion 72. The engagement portion 72 may be configured for connection (e.g., in a securing fashion) with the first end portion 60, such as to at least partially receive one or more of the plurality of teeth 62. The engagement portion 72 may include a first protrusion 74 and/or a second protrusion 76. The first protrusion 74 and/or the second protrusion 76 may extend from the second end portion 70 substantially in the Z-direction. The first protrusion 74 and/or the second protrusion 76 may be configured to contact/engage one or more of the plurality of teeth 62, which may limit relative movement between the first end portion 60 and the second end portion 70 and/or relative movement between the utensil apparatus 20 and the hand 10 of a user. The engagement portion 72 (e.g., the first protrusion 74 and/or the second protrusion 76) may, for example and without limitation, connect with one or more of the plurality of teeth 62 via a snap-fit connection and/or other mechanical friction-fit engagements. The utensil apparatus 20 may be configured to fit to a variety of shapes of the hands 10 of users. For example and without limitation, connecting the teeth 62 in different positions with the engagement portion 72 may result in a utensil apparatus 20 including one or more of a variety of different inner dimensions (e.g., perimeters, circumferences, diameters, etc.) when in the second configuration.

Figure 8:
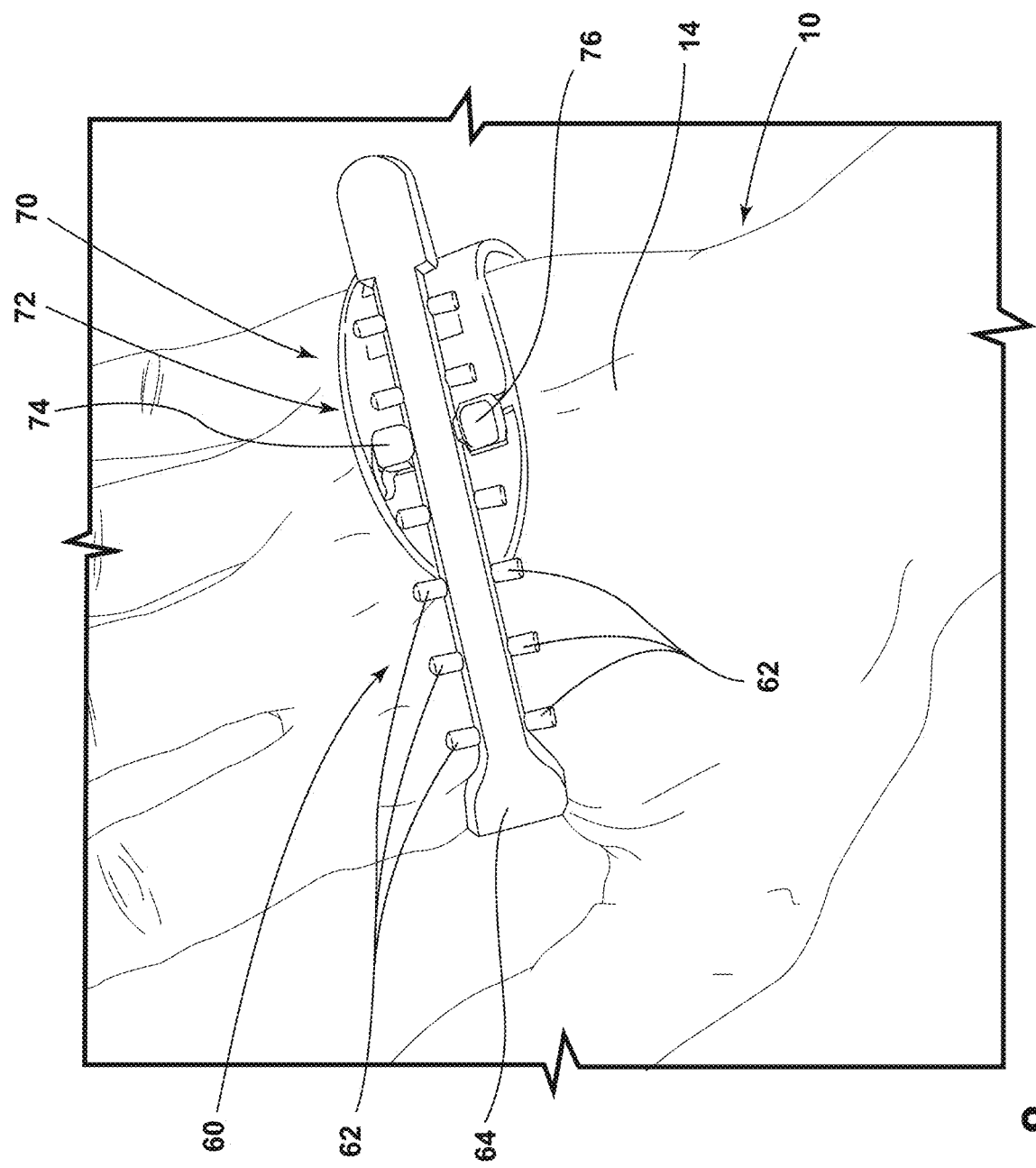
FIG. 8 is a perspective view generally illustrating portions of an embodiment of a utensil apparatus in a second configuration according to teachings of the present disclosure.
Figure 9:
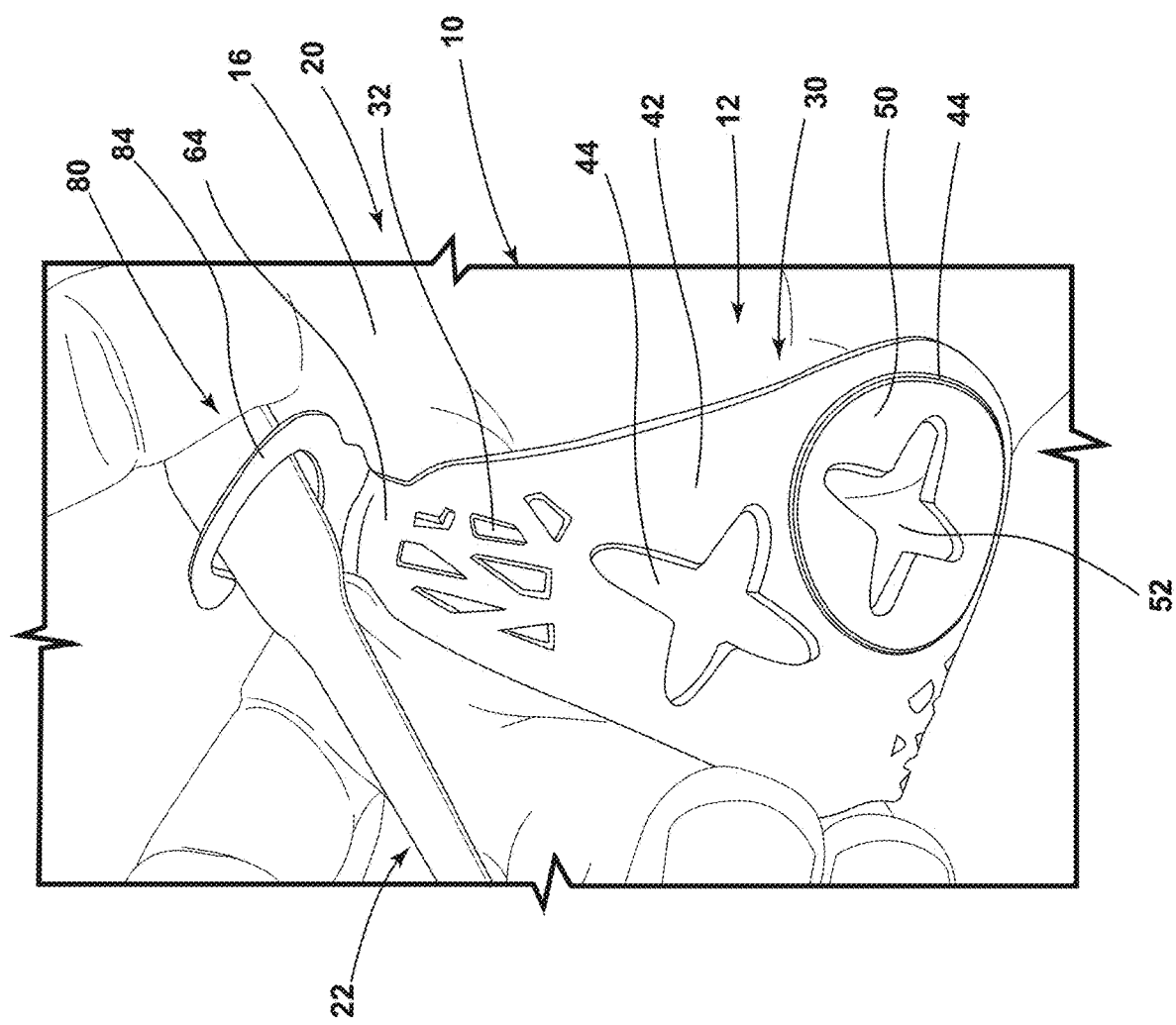
FIG. 9 is a perspective view generally illustrating an embodiment of a utensil apparatus in a second configuration connected to a hand and a utensil according to teachings of the present disclosure.

In examples, the utensil apparatus 20 may include a first configuration (see, e.g., FIGS. 1 and 2) and/or a second configuration (see, e.g., FIGS. 6, 8, and 9). In the first configuration of the utensil apparatus 20, the first end portion 60 may not be engaged with the second end portion 70 (see, e.g., FIGS. 1 and 2A). The body 30, the first end portion 60, and/or the second end portion 70 (e.g., the utensil apparatus 20) may be substantially planar and/or flat (e.g., aligned with a common plane). When changing between the first configuration and the second configuration, the first end portion 60 (e.g., the teeth 62) may engage the second end portion 70 (e.g., the engagement portion 72) to retain the utensil apparatus 20 in the second configuration. A user may bend the first end portion 60 to contact the second end portion 70, and/or a user may bend the second end portion 70 to contact the first end portion 60 (see, e.g., FIG. 8). One or more of the plurality of teeth 62 may be moved into contact with the engagement portion 72 by the user. The user may bend the first end portion 60 to contact the second end portion 70 (e.g., which may be against a material bias of the utensil apparatus 20). For example and without limitation, a user may bend the utensil apparatus 20 from the first configuration to the second configuration. The utensil apparatus 20 may remain in the second configuration if first end portion 60 is connected to the second end portion 70, such as via the one or more teeth 62 engaging the engagement portion 72.

With embodiments, in the second configuration of the utensil apparatus 20, the utensil apparatus 20 may be substantially circular and/or oval-shaped, such as for connection with the hand 10 of a user. The utensil apparatus 20 may be configured to wrap about an outer surface of a hand 10 of a user to form a number of curved shapes and/or configurations. For example and without limitation, the body 30, the first end portion 60, and/or the second end portion 70 may be configured to contact a palm 12 of a hand 10 during use. The utensil apparatus 20 may be configured to contact a first surface (e.g., a palm 12) of a hand 10 and/or a second surface (e.g., a back 14) of a hand 10. In the second configuration, the body 30 may be disposed in contact with and/or substantially aligned with the palm 12 of a user. Additionally or alternatively, in the second configuration, the first end portion 60 and/or the second end portion 70 may be disposed in contact with and/or substantially aligned with the back/top 14 of the hand 10 of a user.

In examples, such as generally illustrated in FIG. 6, the utensil apparatus 20 may be configured such that in the second configuration, one or more fingers (e.g., a small finger 18A, a ring finger 18B, and/or a middle finger 18C) of a user may wrap at least partially around the body 30 to contact a utensil 22 and/or the body 30. For example and without limitation, in a use position of a utensil 22, at least some of the body 30 may be disposed between one or more fingers of the hand 10 and the palm 12 of the hand 10.

Figure 10B:
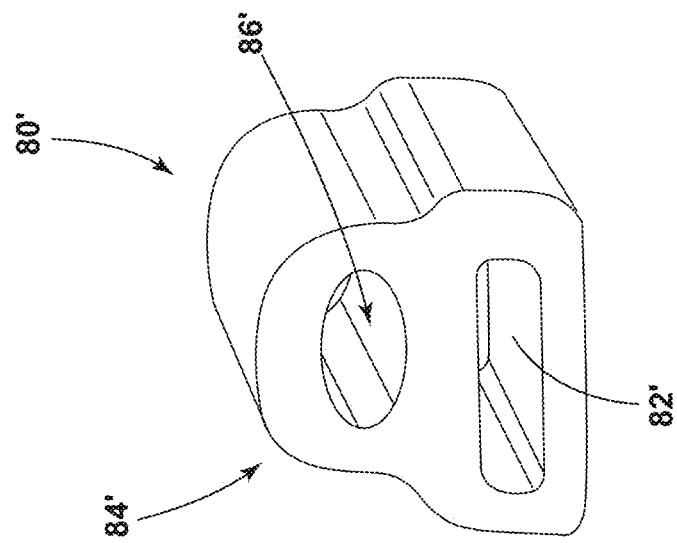
FIGS. 10A and 10B are perspective views generally illustrating portions of embodiments of a flange of a utensil apparatus according to teachings of the present disclosure.
Figure 10A:
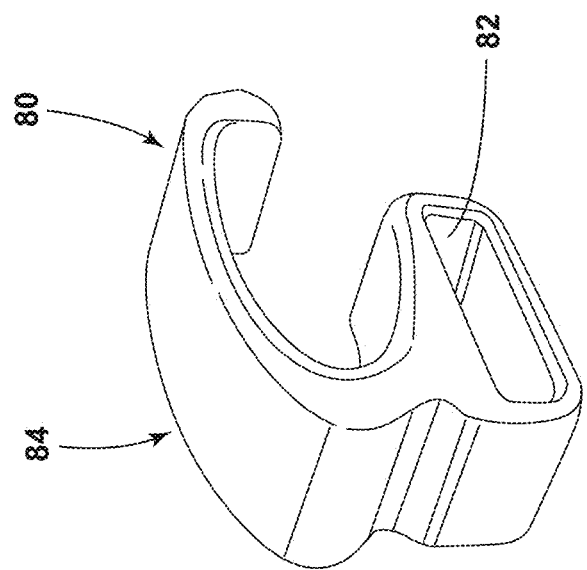

In embodiments, such as generally illustrated in FIGS. 9, 10A, and 10B, the utensil apparatus 20 may include a flange member 80. The flange member 80 may be configured to at least partially limit movement of a utensil 22 that may be used with the utensil apparatus 20. For example and without limitation, the flange member 80 may be configured to contact a handle portion 24 of a utensil 22. The handle portion 24 of the utensil 22 may be substantially planar. Contact between the handle portion 24 and the flange member 80 may connect the utensil 22 to the utensil apparatus 20.

With embodiments, the flange member 80 may be configured to selectively connect with the connection section 64 of the first end portion 60 of the utensil apparatus 20. The flange member 80 may include a flange aperture 82 that may be configured to at least partially receive the first end portion 60 and/or the connection section 64. The flange member 80 may be connected to the utensil apparatus 20 by inserting the first end portion 60 and/or the connection section 64 into the flange aperture 82. The flange member 80 may slide along the first end portion 60 (e.g., in the X-direction) such that the flange member 80 may contact the utensil 22 in one or more of a variety of positions along the connection section 64.

In embodiments, the flange member 80 may include a utensil connection portion 84. The utensil connection portion 84 may extend from the flange member 80 substantially in the Z-direction and/or the Y-direction. The utensil connection portion 84 may include one or more of a variety of shapes, sizes, and/or configurations. For example and without limitation, the utensil connection portion 84 may be substantially curved, hooked, and/or rounded. With embodiments, the utensil connection portion 84' may include an aperture 86' (see, e.g., FIG. 10B). The aperture 86' may be configured to at least partially receive a utensil 22. An inner surface of the utensil connection portion 84' of the flange member 80' may be configured to contact a utensil 22. The inner surface of the aperture 86' may limit movement of the utensil 22 in at least one direction.

With embodiments, a utensil apparatus 20 may include a body 30 including a first portion 40 and/or a second portion 50, a first end portion 60, and/or a second end portion 70. A method of operating the utensil apparatus 20 may include connecting the first end portion 60 with the second end portion 70 such that the body 30, the first end portion 60, and/or the second end portion 70 contact an outer surface of a hand 10 of a user. The method may include inserting a utensil 22 completely through an aperture of the body 30, such as the first aperture 42 or the second aperture 44, such that a portion of the utensil 22 may be in contact with and/or proximate the palm 12 of a hand 10 of the user. The second portion 50 may include a third aperture 52. The method may include connecting a second portion 50 with the first portion 40. Connecting the second portion 50 with the first portion 40 may include connecting the second portion 50 with the second aperture 44. Connecting may include a variety of connections such as a snap-connection and/or a friction-fit connection. Inserting the utensil 22 into through an aperture of the body 30 may include inserting the utensil 22 into the third aperture 52, which may include inserting the utensil 22 through the second aperture 44 (e.g., the utensil 22 may be disposed, simultaneously, in the second aperture 44 and the third aperture 52. The second portion 50 may be configured to rotate within a second aperture 44 of the first portion 40. The third aperture 52 may be configured to receive at least a portion of the utensil 22. The utensil 22 and/or the second portion 50 may rotate within the second aperture 44. The method may include rotating the second portion 50 relative to the first portion 40, such as to provide a different orientation of a utensil 22 relative to the hand 10 of a user.

With examples, such as generally illustrated in FIG. 6, operating a utensil apparatus 20 may include a user applying force to an underside of the utensil 22 via one or more fingers (e.g., a small finger 18A, a ring finger 18B, and/or a middle finger 18C), such as at or about the utensil apparatus 20. This force may be substantially perpendicular to the body 30 of the utensil apparatus 20 and/or to the palm 12 of the user. If a user is unable to apply force, the utensil apparatus 20 may be adjusted for utensils 22 to rest against and/or contact a hand 10 and/or fingers of the user. Additionally or alternatively, operating the utensil apparatus 20 may include the user applying a force to the utensil 22 at or near an operative end of the utensil 22, such as via an index finger 18D of the user. For example and without limitation, the utensil apparatus 20 may permit functional use of a utensil 22 substantially without using a thumb 16. Additionally or alternatively, in examples, such as examples that include a flange member 80, the utensil apparatus 20 may permit functional use of a utensil 22 with a single finger 16, 18A, 18B, 18C, 18D, and/or substantially without using a small finger 18A, a ring finger 18B, a middle finger 18C, and/or an index finger 18D (e.g., just a thumb 16).

In examples, a method of operating a utensil apparatus 20 may include removing the second portion 50 and replacing the second portion 50 with a different second portion, such as the second portion 50' or the second portion 50".

With examples, a utensil 22 may include one or more of a variety of utensils. For example and without limitation, a utensil 22 may include a fork, a knife, a spoon, a pen, a pencil, a stylus, and/or a pointer, among others.

In examples, a utensil apparatus 20 may be configured for use with a left hand of a user and a right hand of a user (e.g., may be reversible/used with either hand). For example and without limitation, when used with a first hand of a user, a first side of the body 30 may be adjacent the palm 12 of the first hand 10 and when used with a second hand of the user, a second/opposite side of the body 30 may be adjacent the palm 12 of the second hand 10 (and the first side may face outward).

Figure 11A:
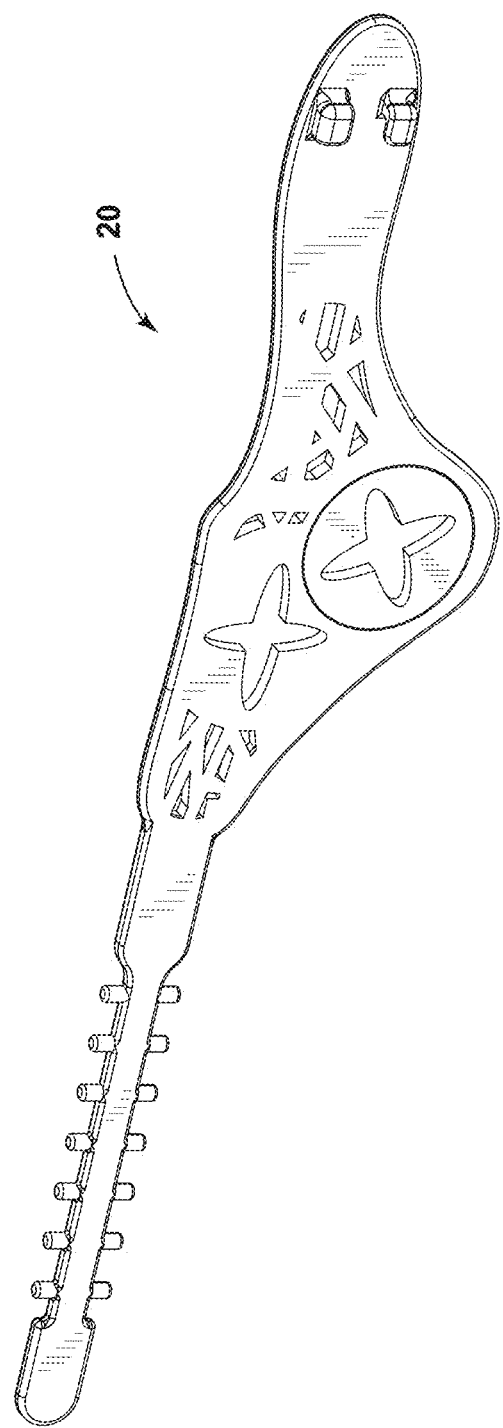
FIG. 11A is a perspective view generally illustrating an embodiment of a utensil apparatus in a first configuration according to teachings of the present disclosure.
Figure 11B:
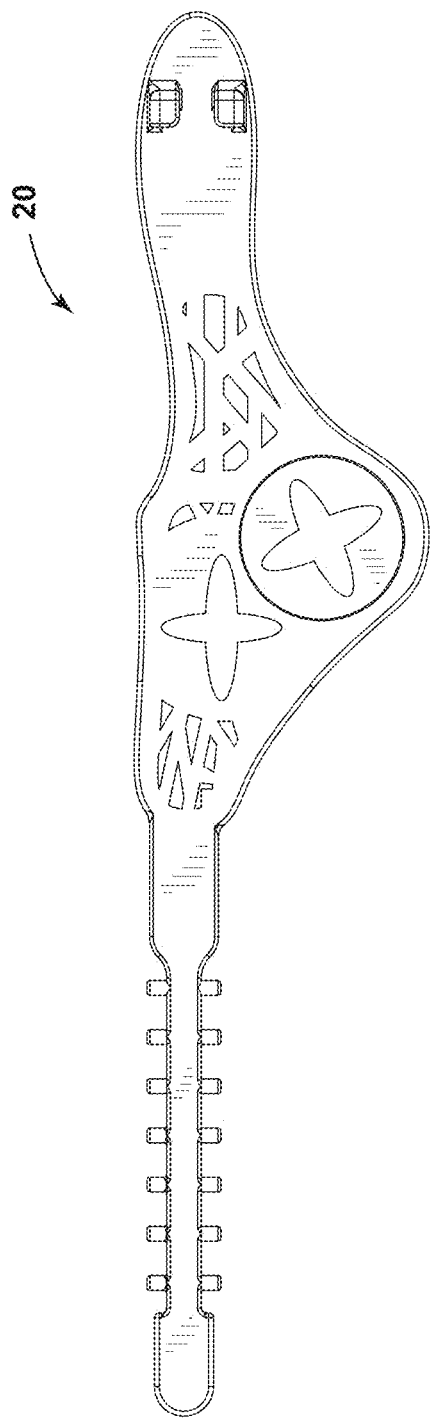
FIG. 11B is a front view of the embodiment of a utensil apparatus of FIG. 11A.
Figure 11C:
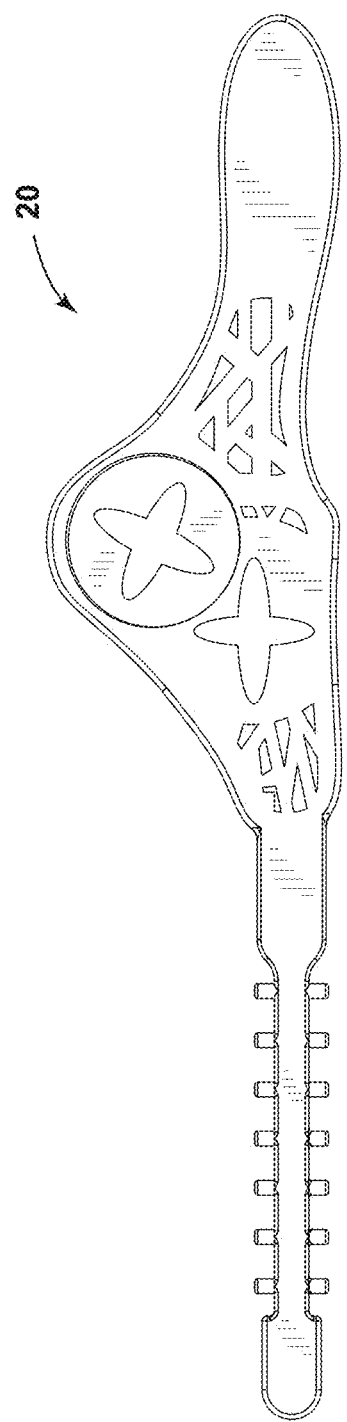
FIG. 11C is a rear view of the embodiment of a utensil apparatus of FIG. 11A.

In embodiments, such as generally illustrated in FIGS. 11A-11G, the utensil apparatus 20 may include a first configuration. FIG. 11A is a perspective view of a utensil apparatus 20 in the first configuration. FIGS. 11B and 11C are front and rear views of the utensil apparatus 20 in the first configuration, respectively. FIGS. 11D and 11E are side views of the utensil apparatus 20 in the first configuration. FIGS. 11F and 11G are top and bottom views of the utensil apparatus 20 in the first configuration, respectively.

Various embodiments are described herein for various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Reference throughout the specification to "various embodiments," "with embodiments," "in embodiments," or "an embodiment," or the like, means that a particular feature, structure, or characteristic described in connection with the embodiment is included in at least one embodiment. Thus, appearances of the phrases "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such element. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of "and" and "or" are to be construed broadly (e.g., to be treated as "and/or"). For example and without limitation, uses of "and" do not necessarily require all elements or features listed, and uses of "or" are intended to be inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

It is intended that all matter contained in the above description or shown in the accompanying drawings shall be interpreted as illustrative only and not limiting. Changes in detail or structure may be made without departing from the present disclosure.

What is claimed is:

1. A utensil apparatus, comprising:
    a body including an aperture configured to receive a utensil;
    a first end portion extending from the body; and
    a second end portion extending from the body;
    wherein the aperture is configured to receive at least a portion of said utensil such that said utensil extends through the aperture; the body is substantially planar; the first end portion is configured to engage the second end portion to connect the body to a hand of a user; the body includes a first portion, a second portion, and a second aperture; and the second portion is disposed at least partially in the second aperture; and
    the second portion is configured to rotate within the second aperture to hold said utensil in a plurality of positions.

2. The utensil apparatus of claim 1, wherein the second portion of the body includes the aperture.

3. The utensil apparatus of claim 2, wherein the first portion of the body includes a third aperture configured to at least partially receive said utensil.

4. The utensil apparatus of claim 1, wherein the aperture is offset from the second aperture in a first direction and a second direction.

5. The utensil apparatus of claim 1, wherein the body is configured to move between a first configuration and a second configuration; the body is substantially flat in the first configuration; and the body is substantially oval-shaped in the second configuration.

6. The utensil apparatus of claim 5, wherein the first end portion includes a plurality of teeth; the second end portion includes an engagement portion; and at least one of the plurality of teeth is configured to engage the engagement portion to maintain the utensil apparatus in the second configuration.

7. The utensil apparatus of claim 1, wherein the utensil apparatus is reversible for use with right and left hands of users.

8. The utensil apparatus of claim 1, including a flange member configured to selectively connect to the first end portion; the first end portion includes a connection section; and
    the flange member is configured to connect to the connection section.

9. A method of operating the utensil apparatus of claim 1, the method comprising:
    connecting the first end portion to the second end portion such that the body is connected to the hand of the user; and
    inserting at least the portion of the utensil into the aperture such that the utensil extends at least partially beyond the body.

10. The method of claim 9, wherein the first portion of the body includes the second aperture; the second portion of the body is disposed in the second aperture; and the second portion includes the aperture.

11. The method of claim 10, wherein inserting at least the portion of the utensil includes inserting at least the portion of the utensil into the second aperture and the aperture.

12. The method of claim 10, including rotating the second portion in the second aperture to provide a different use angle for the utensil.

13. A utensil apparatus, comprising:
a body including an aperture configured to receive a utensil;
a first end portion extending from the body; and
a second end portion extending from the body;
wherein the aperture is configured to receive at least a portion of said utensil such that said utensil extends through the aperture; the body is substantially planar; and the first end portion is configured to engage the second end portion to connect the body to a hand of a user;
wherein the body includes a first portion, a second portion, and a second aperture; and the second portion is disposed at least partially in the second aperture; and
wherein the second portion includes a third aperture; and the third aperture is configured to at least partially receive said utensil.

14. The utensil apparatus of claim 13, wherein the third aperture is substantially X-shaped.

15. The utensil apparatus of claim 13, wherein the third aperture is substantially triangular.

16. A utensil apparatus, comprising:
a body including an aperture configured to receive a utensil;
a first end portion extending from the body; and
a second end portion extending from the body;
wherein the aperture is configured to receive at least a portion of said utensil such that said utensil extends through the aperture; the body is substantially planar; and the first end portion is configured to engage the second end portion to connect the body to a hand of a user;
wherein the body includes a first portion, a second portion, and a second aperture; and the second portion is disposed at least partially in the second aperture; and
wherein the second portion includes a channel configured to at least partially receive a radial flange of the first portion for rotatably connecting the second portion with the first portion.

17. The utensil apparatus of claim 16, wherein the channel is at least partially defined between a first flange portion of the second portion and a second flange portion of the second portion; and wherein the first flange portion includes a smaller diameter than the second flange portion.

18. The utensil apparatus of claim 16, wherein the second portion includes the aperture.

19. A utensil apparatus, comprising:
a body including an aperture;
a plurality of interchangeable disks configured for selective connection with the body via the aperture;
a first end portion extending from the body; and
a second end portion extending from the body;
wherein the plurality of interchangeable disks include respective second apertures configured to receive at least a portion of a utensil such that said utensil extends through the respective second apertures; the body is substantially planar; and the first end portion is configured to engage the second end portion to connect the body to a hand of a user.

20. A utensil apparatus, comprising:
a body including an aperture configured to receive a utensil;
a first end portion extending from the body;
a second end portion extending from the body; and
a flange member configured to selectively connect to the first end portion;
wherein the aperture is configured to receive at least a portion of said utensil such that said utensil extends through the aperture;
the body is substantially planar;
the first end portion is configured to engage the second end portion to connect the body to a hand of a user;
the first end portion includes a connection section;
the flange member is configured to connect to the connection section;
the flange member includes a utensil connection portion and a flange aperture;
the flange aperture is configured to receive the first end portion; and
the utensil connection portion is configured to at least partially receive said utensil.

* * * * *